(12) United States Patent
Au (10) Patent No.: US 10,856,737 B2
(45) Date of Patent: Dec. 8, 2020

(54) FLEXIBLE PRESSURE-SENSING PAD AND MANUFACTURING METHOD

(71) Applicant: CONTIN TECHNOLOGY LIMITED, Shatin (HK)

(72) Inventor: Chungwing Au, Shenzhen (CN)

(73) Assignee: CONTIN TECHNOLOGY LIMITED, Shatin (HK)

( * ) Notice: Subject to any disclaimer, the term of this patent is extended or adjusted under 35 U.S.C. 154(b) by 0 days.

(21) Appl. No.: 16/465,062

(22) PCT Filed: Jul. 20, 2018

(86) PCT No.: PCT/CN2018/096440
§ 371 (c)(1),
(2) Date: May 29, 2019

(87) PCT Pub. No.: WO2019/019956
PCT Pub. Date: Jan. 31, 2019

(65) Prior Publication Data
US 2019/0290132 A1 Sep. 26, 2019

(30) Foreign Application Priority Data
Jul. 24, 2017 (CN) .......................... 2017 1 0607459

(51) Int. Cl.
*G01L 1/00* (2006.01)
*G01L 5/00* (2006.01)
(Continued)

(52) U.S. Cl.
CPC ............ *A61B 5/0053* (2013.01); *A47C 27/12* (2013.01); *A47C 31/123* (2013.01);
(Continued)

(58) Field of Classification Search
CPC ................ A61B 5/0053; A61B 5/6843; A61B 2562/0247; A47C 27/12; A47C 31/123; A47C 31/126; G01L 1/20; G01L 5/00
(Continued)

(56) References Cited

U.S. PATENT DOCUMENTS

| 4,149,066 A * | 4/1979 | Niibe ....................... H05B 3/36 219/212 |
| 6,504,531 B1 | 1/2003 | Sandbach |

(Continued)

FOREIGN PATENT DOCUMENTS

| CN | 2816775 Y | 9/2006 |
| CN | 201219071 Y | 4/2009 |

(Continued)

*Primary Examiner* — Max H Noori
(74) *Attorney, Agent, or Firm* — Muncy, Geissler, Olds & Lowe, P.C.

(57) ABSTRACT

The present invention relates to a flexible pressure-sensing pad and manufacturing method thereof. The flexible pressure-sensing pad includes a first fabric substrate layer, a second fabric substrate layer, and a fabric barrier layer provided between the first fabric substrate layer and the second fabric substrate layer. The first fabric substrate layer includes a first electrode and the second fabric substrate layer includes a second electrode. The fabric barrier layer has multiple through holes. The first electrode and the second electrode are electrically connected with a controller. Compared with the current pressure-sensing pad, the present invention is thinner and more flexible, has superior breathability and waterproofness, does not generate an irritating noise, creates a quiet recuperative environment for patients and can sense an external force over the entire pressure sensing pad without any blind spots, thereby providing better user experience.

16 Claims, 5 Drawing Sheets

(51) Int. Cl.
  *A61B 5/00* (2006.01)
  *G01L 1/20* (2006.01)
  *A47C 27/12* (2006.01)
  *A47C 31/12* (2006.01)

(52) U.S. Cl.
  CPC .......... *A47C 31/126* (2013.01); *A61B 5/6843* (2013.01); *G01L 1/20* (2013.01); *G01L 5/00* (2013.01); *A61B 2562/0247* (2013.01)

(58) Field of Classification Search
  USPC .......................................................... 73/774
  See application file for complete search history.

(56) References Cited

U.S. PATENT DOCUMENTS

| | | | | |
|---|---|---|---|---|
| 2003/0090200 A1* | 5/2003 | Topelberg | ............... | H05B 33/26 313/511 |
| 2005/0095934 A1* | 5/2005 | Serban | ................. | G06F 3/0221 442/110 |
| 2005/0235482 A1* | 10/2005 | Deaett | ................... | H01P 11/00 29/600 |
| 2010/0305484 A1* | 12/2010 | Grollier | ................. | A45D 44/22 601/84 |
| 2012/0193205 A1* | 8/2012 | Jiang | .................... | G06F 3/0202 200/5 A |
| 2014/0001433 A1* | 1/2014 | Ruekes | ............. | H01L 29/1606 257/9 |
| 2014/0150573 A1 | 6/2014 | Cannard et al. | | |
| 2015/0301603 A1* | 10/2015 | Maggiali | ................ | G06F 3/044 345/174 |
| 2017/0146413 A1* | 5/2017 | Ibrocevic | ................. | F16P 3/12 |

FOREIGN PATENT DOCUMENTS

| | | |
|---|---|---|
| CN | 102438520 A | 5/2012 |
| CN | 202632474 U | 12/2012 |
| CN | 202711422 U | 1/2013 |
| CN | 203204788 U | 9/2013 |
| CN | 203720987 U | 7/2014 |
| CN | 107432613 A | 12/2017 |

* cited by examiner

FLEXIBLE PRESSURE-SENSING PAD AND MANUFACTURING METHOD

FIELD OF INVENTION

The present invention relates to a medical equipment technology, particularly to a flexible pressure-sensing pad and a manufacturing method thereof.

BACKGROUND

Figure 1:
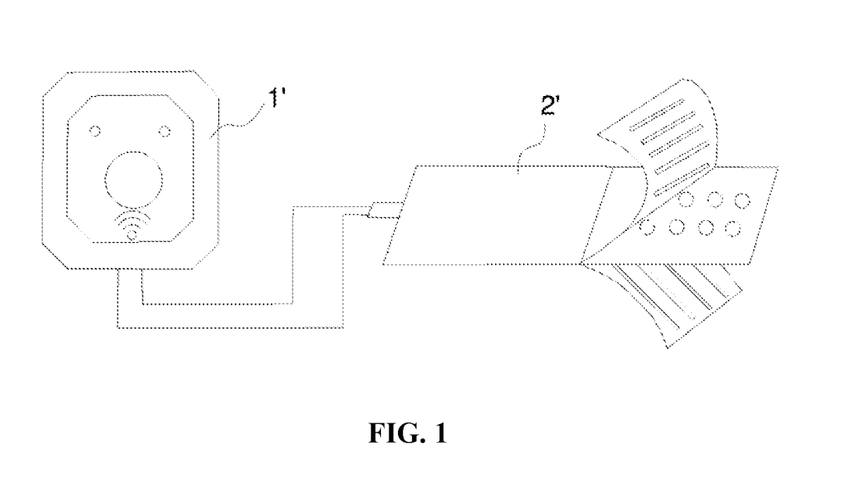
FIG. 1 is a structural schematic view of a pressure-sensing pad in current technologies.

At mental hospitals, nursing homes for the elderly, children's hospitals and other medical institutions or homes, it is necessary to monitor the activities and positions of the people being cared (such as patients). However, as medical institutions are busy, nurses may overlook some patients due to large number of people to be cared. Therefore, user monitoring devices are widely applied at medical institutions to monitor the activities of the people being cared and alleviate the pressure of nurses. Currently, user monitoring devices will alert the staffs or nurses or caregiver when users leave their beds or chairs. As shown in FIG. 1, a typical monitoring system comprises a controller 1' and a pressure pad 2', and the controller may be used to receive signals from the pressure pad.

Figure 2:
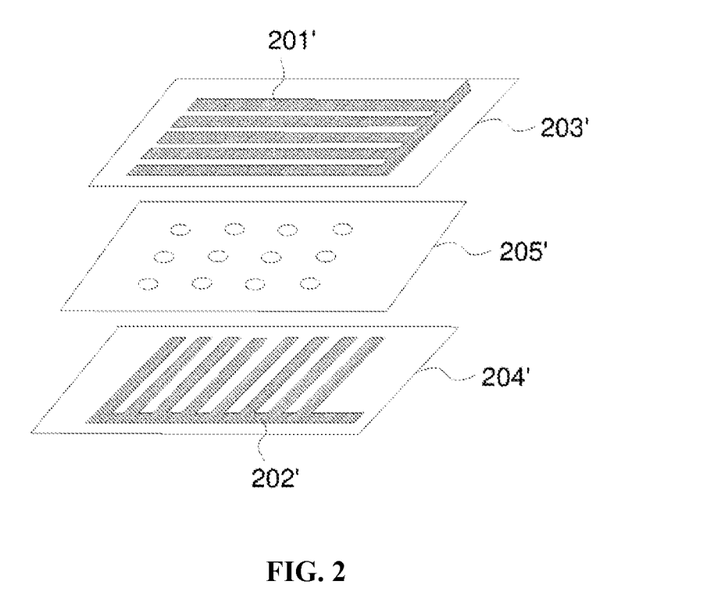
FIG. 2 is a structural schematic view of a pressure pad in current technologies.

As shown in FIG. 2, a typical pressure pad comprises two groups of parallel electrodes, including a first electrode 201' and a second electrode 202', which are on a first plastic film 203' and a second plastic film 204' respectively. The electrodes and the plastic films are both directed at a right angle, while a barrier layer 205' is provided between the electrodes and typically is made of a material with high resistance, such as a foam material or a cardboard, and multiple through holes are provided in the middle of the barrier layer. Under the condition of no external force, the barrier layer provides high resistance between the first electrode and the second electrode and forms an open circuit. Contrarily, under the condition of an external force, the plastic films will be connected via the through holes of the barrier layer. At the same time, the first electrode and the second electrode will form a closed circuit, trigger a sensing pad and send signals.

However, the existing pressure pad has following defects: (1) the substrate of the pressure pad is a plastic film, for example made of polyvinyl chloride (PVC) or polyethylene terephthalate (PET). These materials typically are flexible, bendable and waterproof, but their breathability is poor, making sweat condensed on the sensing pad. Another problem of these plastic films is an irritating noise generated when the user adjusts his/her posture or position.

(2) Further, the existing barrier layer is designed to have multiple through holes in various shapes in the middle of a foam material or a cardboard (>10 mm). It should be thick enough to block electrodes on two sides, resulting in a thick and heavy sensing pad. Further, a limited number of through holes make many locations of the pressure pad insensitive (blind spots) to external forces. These problems result in a poor user experience and dampen user's interest in using the sensing pad.

SUMMARY OF THE INVENTION

In order to overcome the defects of current technologies, an objective of the present invention is to provide a flexible pressure-sensing pad. The flexible pressure-sensing pad uses fabric, which has a flexible structure and does not generate a noise when being folded, to replace the original plastic film as a substrate, and the barrier layer is also made of fabric. Compared with an existing pressure-sensing pad, the flexible pressure-sensing pad provided by the present invention is thinner and more flexible, has superior breathability and waterproofness, does not generate an irritating noise, creates a quiet recuperative environment for patients and can sense an external force over the entire pressure sensing pad without any blind spots, thereby providing better user experience.

A first objective of the present invention is achieved by employing the following technical solution: a flexible pressure-sensing pad, comprising a first fabric substrate layer, a second fabric substrate layer, and a fabric barrier layer provided between the first fabric substrate layer and the second fabric substrate layer; the first fabric substrate layer comprises a first electrode on a side facing the fabric barrier layer, and the second fabric substrate layer comprises a second electrode on a side facing the fabric barrier layer; the fabric barrier layer is provided with multiple through holes; the first electrode and the second electrode are electrically connected with a controller.

Further, the first fabric substrate layer and the second fabric substrate layer are two separate fabrics in a same size with one being superimposed on the other, or are one fabric folded symmetrically from a middle line of the fabric.

Further, fabrics for the first fabric substrate layer and the second fabric substrate layer are one of flexible or bendable synthetic textile, vegetable textile, animal textile and mineral textile.

Further, the first electrode covers a lower surface of the first fabric substrate layer, and the second electrode covers an upper surface of the second fabric substrate layer; or the first electrode is distributed on the lower surface of the first fabric substrate layer in a form of parallel lines, cross lines or grid lines, and the second electrode is distributed on the upper surface of the second fabric substrate layer in a form of parallel lines, cross lines or grid lines.

Further, the first electrode and the second electrode both are formed by applying a conductive material to the first fabric substrate layer and the second fabric substrate layer; further, the conductive ink is metal Ag, metal Cu, metal Au, carbon and conductive polymer or a composition of more than one of them; the solid flexible conductive material is a conductive fabric or a thin metal strap.

Further, the fabric barrier layer is 0.01 mm-10 mm thick; the through holes of the fabric barrier layer are round holes, triangular holes, rectangular holes, pentagonal holes, hexagonal holes or irregular holes, or a combination of more than one of them.

Further, the flexible pressure-sensing pad further comprises a first flexible film provided between the first fabric substrate layer and the first electrode, and a second flexible film provided between the second fabric substrate layer and the second electrode.

Further, the first flexible film and the second flexible film are 10 μm-500 μm thick thermoplastic films; the thermoplastic films are made of one of TPU, PET and PE.

Further, the flexible pressure-sensing pad further comprises a third flexible film provided around an edge of the first fabric substrate layer and around an edge of the second fabric substrate layer, as a sealing edge cover.

A second objective of the present invention is achieved by employing the following technical solution: a manufacturing method of a flexible pressure-sensing pad, comprising, laminating a first flexible film on a first fabric substrate layer, and a second flexible film on a second fabric substrate layer;

laminating a first electrode on the first flexible film away from the first fabric substrate layer, and a second electrode on the second flexible film away from the second fabric substrate layer;

connecting a cable with the first electrode and the second electrode;

assembling the first fabric substrate layer laminated with the first flexible film and the first electrode, a fabric barrier layer, and the second fabric substrate layer laminated with the second flexible film and the second electrode.

Further, the manufacturing method of a pressure-sensing pad further comprises providing a first fabric substrate layer and a second fabric substrate layer. The step of providing comprises: preparing a fabric, cleaning the fabric, then cutting the fabric into two fabrics of a same shape and a same size as a first fabric substrate layer and a second fabric substrate layer respectively, with the fabric barrier layer being between the first electrode and the second electrode; or, using a fabric and symmetrically folding the fabric from a middle line to form the first fabric substrate layer and the second fabric substrate layer.

Further, the step of laminating a first flexible film on a first fabric substrate layer, and a second flexible film on a second fabric substrate layer comprises: pasting thermoplastic films on a lower surface of the first fabric substrate layer and an upper surface of the second fabric substrate layer respectively.

Further, the step of laminating a first electrode on the first flexible film away from the first fabric substrate layer, and the second electrode on the second flexible film away from the second fabric substrate layer comprises: applying conductive ink to the lower surface of the first fabric substrate layer and the upper surface of the second fabric substrate layer by an adhesive or silk-screen printing to form a first electrode and a second electrode; or, printing a solid flexible conductive material to the lower surface of the first fabric substrate layer and the upper surface of the second fabric substrate layer by an adhesive or hot pressing or silk-screen printing to form the first electrode and the second electrode.

Further, the step of connecting a cable with the first electrode and the second electrode comprises: using a copper strip with adhesive/a conductive fabric with adhesive to fix the cable to the first electrode, and using a copper strip with adhesive/a conductive fabric with adhesive to fix the cable to the second electrode; or, opening eyeholes/eyelets on the first electrode and the second electrode, and fixing the cable to the first electrode or the second electrode via fixing parts and the eyeholes/eyelets.

Further, the step of assembling the first fabric substrate layer laminated with the first flexible film and the first electrode, the fabric barrier layer, and the second fabric substrate layer laminated with the second flexible film and the second electrode comprises: placing the barrier layer between the first fabric substrate layer and the second fabric substrate layer, aligning edges of the first fabric substrate layer and the second fabric substrate layer or the first electrode and the second electrode; and then fixing the first fabric substrate layer coated with the first flexible film and the first electrode, the second fabric substrate layer coated with the second flexible film and the second electrode, and the barrier layer together.

Compared with current technologies, the present invention has the following beneficial effect: the flexible pressure-sensing pad provided by the present invention uses fabric, which has a flexible structure and does not generate a noise when being folded, to replace the original plastic film as a substrate, and the barrier layer is also made of fabric. Compared with an existing pressure-sensing pad, the flexible pressure-sensing pad provided by the present invention is thinner and more flexible, has superior breathability and waterproofness, does not generate an irritating noise, creates a quiet recuperative environment for patients and can sense an external force over the entire pressure sensing pad without any blind spots, thereby providing better user experience.

In the figures: 1': controller; 2': pressure pad; 201': first electrode; 202': second electrode; 203': first plastic film; 204': second plastic film; 205': barrier layer; 1: first fabric substrate layer; 2: second fabric substrate layer; 3: fabric barrier layer; 30: through hole; 4: first electrode; 5: second electrode; 6: cable.

DETAILED DESCRIPTION

The present invention will be further described with reference to accompanying drawings and implementation manners below. It should be noted that the embodiments or technical features may be freely combined into new embodiments under the precondition of no conflict.

As shown in FIG. 3~FIG. 11, a flexible pressure-sensing pad comprises a first fabric substrate layer 1 and a second fabric substrate layer 2 as substrates of the pressure pad, and a fabric barrier layer 3 provided between the first fabric substrate layer 1 and the second fabric substrate layer 2; the first fabric substrate layer 1 is combined with a first electrode 4 on a side facing the fabric barrier layer 3, and the second fabric substrate layer 2 is combined with a second electrode 5 on a side facing the fabric barrier layer 3; the fabric barrier layer 3 is provided with multiple through holes 30; the first electrode 4 and the second electrode 5 are electrically connected with a controller (not shown in the figure). The cable 6 is fixed on the first fabric substrate layer 1 or the second fabric substrate layer 2 to endure a tensile force as high as 200N. After fixation, a connection force between the first electrode 4 or the second electrode 5 and the cable 6 should be able to endure a force of above 10N, preferably 50N, most preferably 100N or above. Open circuit resistance of the electrodes should be greater than 1MΩ most preferably greater than 10MΩ Closed circuit resistance should be smaller than 1MΩ most preferably smaller than 10 kΩ.

Figure 3:
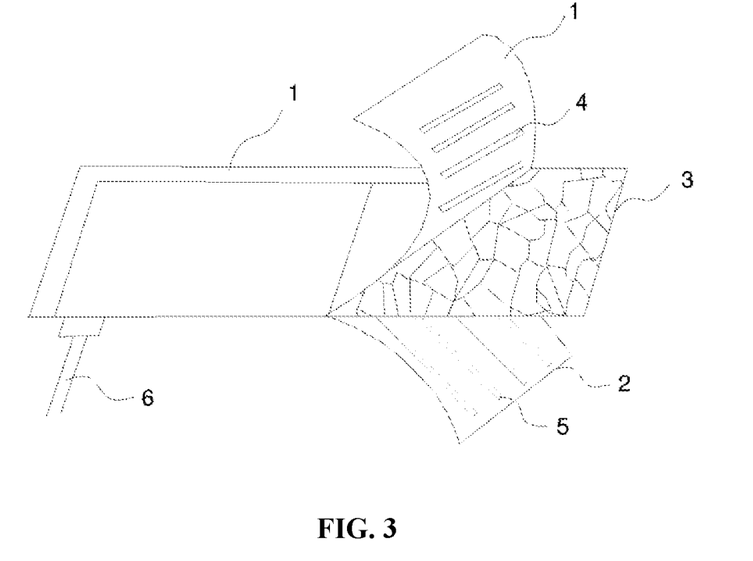
FIG. 3 is a structural schematic view of a flexible pressure-sensing pad according to Embodiment 1 of the present invention.

Operating principle: without an external force, the first electrode 4 and the second electrode 5 will not contact each other to form an open circuit. When an external force greater than a threshold value is applied on surfaces of the substrates, the first electrode 4 and the second electrode 5 will contact each other via the through holes 30 of the fabric barrier layer 3 to form a closed circuit and send signals.

The flexible pressure-sensing pad provided by the present invention uses fabric, which has a flexible structure and does not generate a noise when being folded, to replace the original plastic film as a substrate, and the barrier layer is also made of fabric. Compared with an existing pressure-sensing pad, the flexible pressure-sensing pad provided by the present invention is thinner and more flexible, has superior breathability and waterproofness, does not generate an irritating noise, creates a quiet recuperative environment for patients and can sense an external force over the entire pressure sensing pad without any blind spots, thereby providing better user experience.

The flexible pressure-sensing pad provided by the present application uses a fabric as a substrate. The fabric may be natural textile or synthetic textile, and has superior breathability and waterproofness. As a preferred solution of the present application, the fabric for the first fabric substrate layer 1 and the second fabric substrate layer 2 is one of flexible or bendable synthetic textile, vegetable textile, animal textile and mineral textile.

Figure 4:
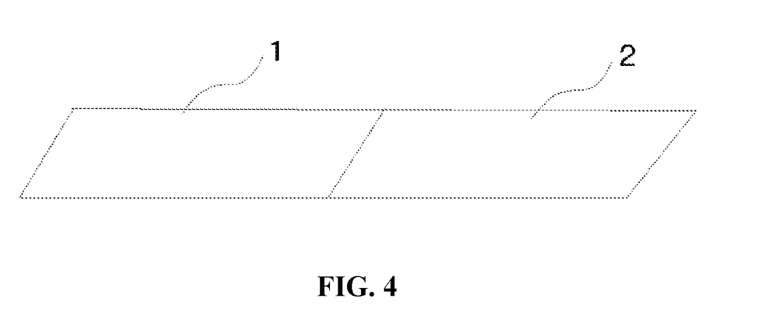
FIG. 4 is a structural schematic view of substrates in a flexible pressure-sensing pad according to Embodiment 2 of the present invention.
Figure 5:
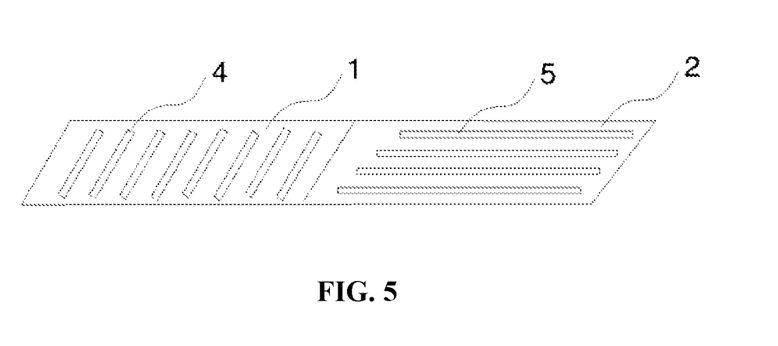
FIG. 5 is a structural schematic view of substrates and electrodes in a flexible pressure-sensing pad according to Embodiment 2 of the present invention.
Figure 6:
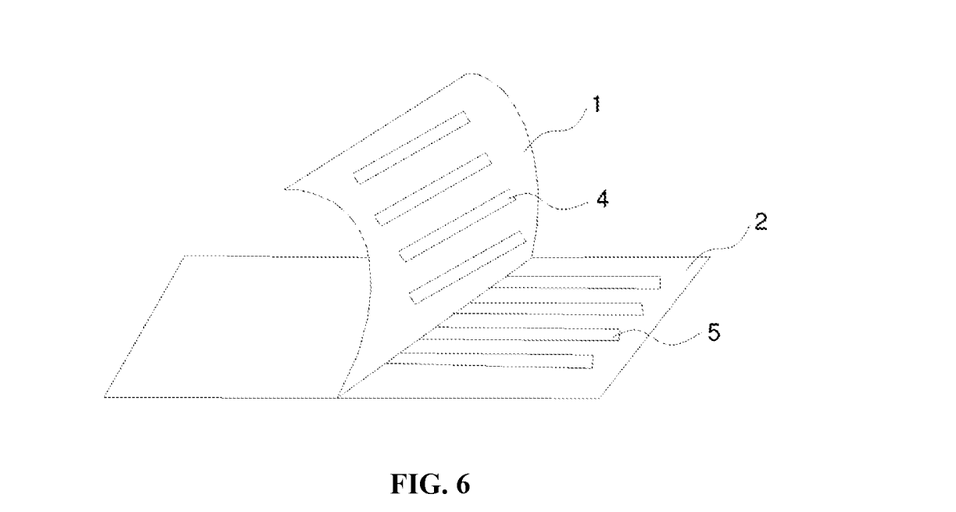
FIG. 6 is a structural schematic view of folded substrates in a flexible pressure-sensing pad according to Embodiment 2 of the present invention.
Figure 7:
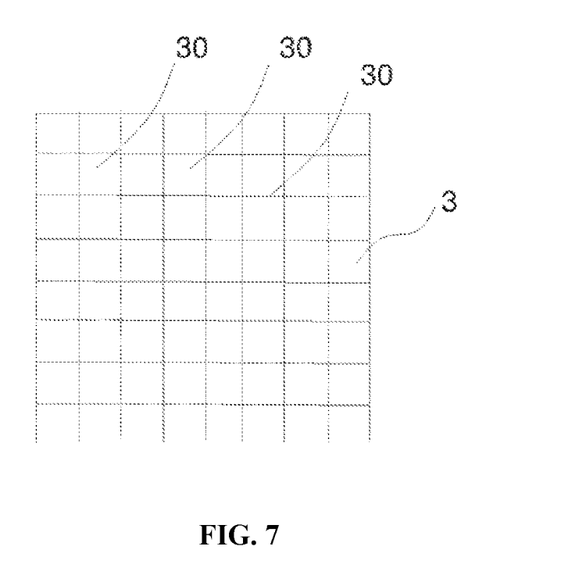
FIG. 7 is a structural schematic view of a fabric barrier layer in a flexible pressure-sensing pad according to a preferred embodiment of the present invention (the through holes are square)
Figure 8:
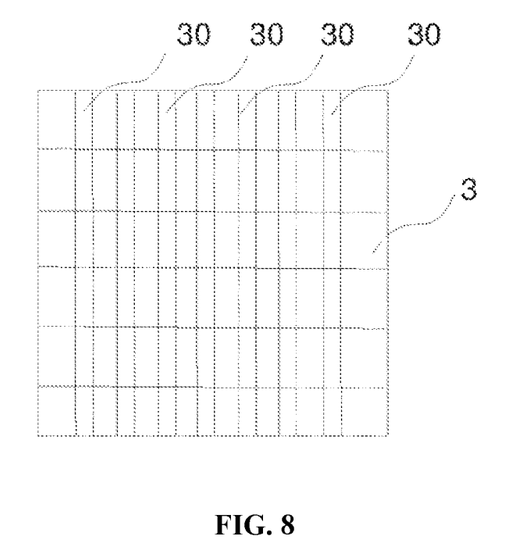
FIG. 8 is a structural schematic view of a fabric barrier layer in a flexible pressure-sensing pad according to a preferred embodiment of the present invention (the through holes are rectangular)
Figure 9:
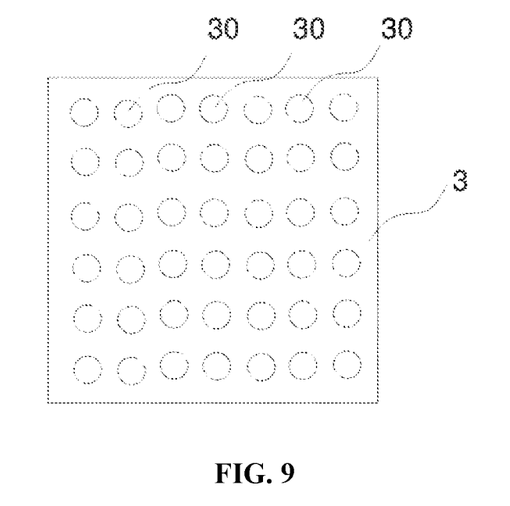
FIG. 9 is a structural schematic view of a fabric barrier layer in a flexible pressure-sensing pad according to a preferred embodiment of the present invention (the through holes are round)
Figure 10:
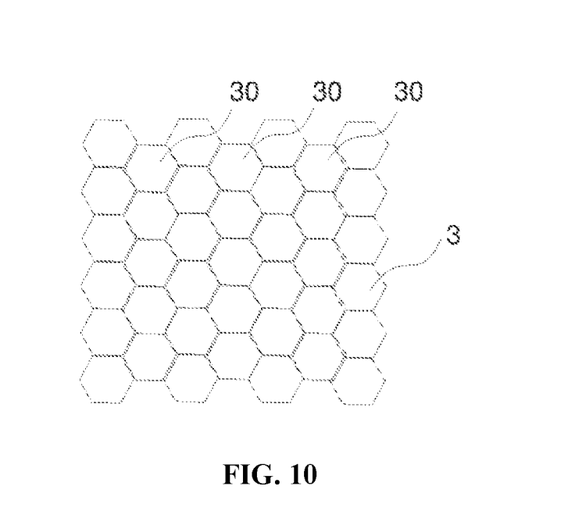
FIG. 10 is a structural schematic view of a fabric barrier layer in a flexible pressure-sensing pad according to a preferred embodiment of the present invention (the through holes are hexagonal)
Figure 11:
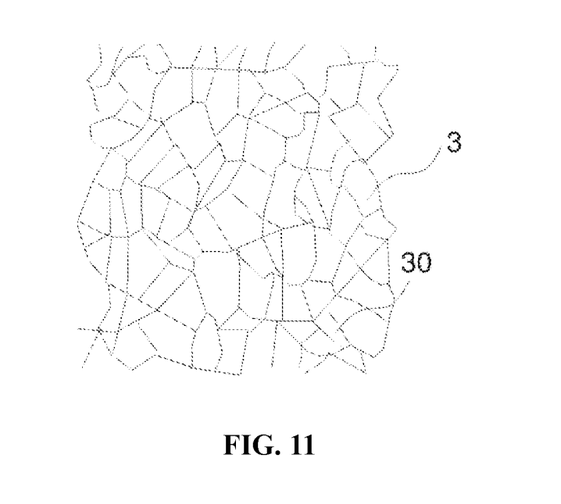
FIG. 11 is a structural schematic view of a fabric barrier layer in a flexible pressure-sensing pad according to a preferred embodiment of the present invention (the through holes are irregular)

There are two ways to connect the first fabric substrate layer 1 and the second fabric substrate layer 2 in the present application. The first way: as shown in FIG. 3, the first fabric substrate layer 1 and the second fabric substrate layer 2 are formed by two separate fabrics in a same size with one being superimposed on the other. The second way: as shown in FIG. 4~FIG. 6, the first fabric substrate layer 1 and the second fabric substrate layer 2 are formed by one fabric, which is folded symmetrically from a middle line of the fabric.

There are many ways to connect the first electrode 4 with the first fabric substrate layer 1 and connect the second electrode 5 with the second fabric substrate layer 2 in the present application. The first way: the first electrode 4 covers a lower surface of the entire first fabric substrate layer 1, and the second electrode 5 covers an upper surface of the entire second fabric substrate layer 2; the second method: the first electrode 4 is formed in different patterns, i.e., is distributed on a lower surface of the first fabric substrate layer 1 in a form of parallel lines, cross lines, or parallel lines, regular grid lines or cross lines connected via cross lines, and the second electrode 5 is formed in different patterns, i.e., is distributed on an upper surface of the second fabric substrate layer 1 in a form of parallel lines, cross lines, or parallel lines, regular grid lines or cross lines connected via cross lines. If an interlaced pattern is used, there will be following advantages: a) reduce false alarms (triggered by accidental folding of the pressure-sensing pad or by a pillow or blanket falling by accident) because crossed circuits will form a closed circuit only when two cross lines are contacted and connected at the same time; b) adjusting an activation threshold of the sensing pad by changing a width of the cross lines and a space between them.

As a preferred solution of the present application, the first electrode 4 and the second electrode 5 both are formed by applying a conductive material onto the first fabric substrate layer 1 and the second fabric substrate layer 2; the conductive material is conductive ink printed on the first fabric substrate layer 1 and the second fabric substrate layer 2 or a solid flexible conductive material adhered to the first fabric substrate layer 1 and the second fabric substrate layer 2. The conductive ink is metal Ag, metal Cu, metal Au, carbon or conductive polymer (such as PEDOT or PSS) or a composition of more than one of them; the solid flexible conductive material is a conductive fabric or a thin metal strap.

When there is not an external force, the fabric barrier layer 3 is used to separate the first and second electrodes 5, avoid contact and prevent formation of a closed circuit. As shown in FIG. 7~FIG. 11, the fabric barrier layer 3 in the present application uses a fabric mesh with regular or irregular through holes 30. Firstly, as the fabric mesh typically is thin and very flexible, a sensing pad made of a fabric mesh is concise, has good flexibility and may be folded into any shape. Secondly, as most part of the fabric mesh is distributed with through holes 30, a sensing pad made of a fabric mesh has fewer or almost does not have "blind spots". Thirdly, as these fabric meshes are very thin, they can be easily fixed to a substrate by means of polymer (such as TPU) welding or adhesive. This approach will simplify the manufacturing process and reduce reliability problems caused by relocation of the fabric barrier layer 3 in an existing sensing pad.

As a preferred solution of the present application, the fabric barrier layer 3 is 0.01 mm-10 mm thick; the through holes 30 of the fabric barrier layer 3 are round holes, triangular holes, rectangular holes, pentagonal holes, hexagonal holes or irregular holes, or a combination of more than one of them.

As a preferred solution of the present application, the flexible pressure-sensing pad further comprises a first flexible film covering a lower surface of the first fabric substrate layer 1, and a second flexible film covering an upper surface of the second fabric substrate layer 2. The first flexible film and the second flexible film are 10 μm-500 μm thick thermoplastic films; the thermoplastic films are one of thermoplastic polyurethane (TPU) films, polyethylene terephthalate (PET) films, polyethylene (PE) films and other films. The first flexible film and the second flexible film may fully cover the lower surface of the first fabric substrate layer 1 and the upper surface of the second fabric substrate layer 2 respectively, and a third flexible film is partially provided around an edge of the first fabric substrate layer 1 and around an edge of the second fabric substrate layer 2 respectively, as a sealing edge cover. If thermoplastic films are used, they have following advantages: a) raise a waterproof ability of the pressure-sensing pad and protection of electrodes; b) help fix loose wires or yarns to a substrate; c) serve as an adhesive (when heated) to fix the fabric barrier layer 3 to fabric substrate layers; d) serve as a sealing material (when heated) to seal the edge of the sensing pad.

The thermoplastic films may be constructed by means of spraying a polymer liquid, or welding, or pressing a plastic film.

The present invention further provides a manufacturing method of a flexible pressure-sensing pad, comprising, a step of preparing a substrate layer fabric: preparing a fabric, cleaning the fabric, then cutting the fabric into two fabrics of a same shape and a same size as a first fabric substrate layer 1 and a second fabric substrate layer 2 respectively;

or, using a fabric and symmetrically folding the fabric from a middle line to form the first fabric substrate layer 1 and the second fabric substrate layer 2;

a step of constructing a flexible film: pasting thermoplastic films on a lower surface of the first fabric substrate layer 1 and an upper surface of the second fabric substrate layer 2 respectively;

a step of constructing electrodes: applying conductive ink to the lower surface of the first fabric substrate layer 1 and the upper surface of the second fabric substrate layer 2 by means of adhesive or silk-screen printing to form electrodes; or, applying a solid flexible conductive material, which is a conductive fabric or a metal strap, to the lower surface of the first fabric substrate layer 1 and the upper surface of the second fabric substrate layer 2 by means of adhesive or hot pressing or silk-screen printing to form electrodes;

a step of connecting an cable 6: using a copper strip with adhesive/a conductive fabric with adhesive to fix the cable 6 to the first electrode 4, and using a copper strip with adhesive/a conductive fabric with adhesive to fix the cable 6 to the second electrode 5;

or, opening eyeholes/eyelets on the first electrode 4 and the second electrode 5, and fixing the cable 6 to the first electrode 4 or the second electrode 5 via fixing parts and the eyeholes/eyelets.

a step of preparing a fabric barrier layer 3: preparing a fabric with mesh openings, as a fabric barrier layer 3;

a step of assembling: placing the fabric barrier layer 3 between the first fabric substrate layer 1 and the second fabric substrate layer 2, and aligning edges of the first fabric substrate layer and the second fabric substrate layer (if the first fabric substrate layer and the second fabric substrate layer 2 are a same fabric, alignment of edges or alignment of the first electrode 4 and the second electrode 5 may be achieved by folding the fabric along a middle line. If the first fabric substrate layer 1 and the second fabric substrate layer 2 are two separate fabrics, alignment may be achieved by putting the second fabric substrate layer 2 at the top of the first fabric substrate layer 1 and aligning edges, or by aligning the first electrode 4 with the second electrode 5, and then fixing the first fabric substrate layer 1 coated with the first flexible film and the first electrode 4, and the second fabric substrate layer 2 and the fabric barrier layer 3 coated with the second flexible film and the second electrode 5 together. The fixing method is as follows: a) conducting hot pressing and high frequency welding and then carrying out an edge processing procedure; b) applying adhesive and then carry out edge processing; c) processing edges by means of seaming. Edge processing may include seaming, seam sorting, trimming, mechanical cutting and laser cutting.

Embodiment 1: A Flexible Pressure-Sensing Pad, as Shown in FIG. 3

The flexible pressure-sensing pad is manufactured by a following method:

Preparing a substrate layer fabric: In this embodiment, two fabrics in a size of 800 mm×500 mm are used as a first fabric substrate layer 1 and a second fabric substrate layer 2 respectively, each fabric has a front side and a back side, a smooth surface is used to form an external surface of a sensing pad, and a relatively coarse surface is used to form an internal surface of the sensing pad.

a step of constructing a flexible film: hot pressing a layer of TPU (100 μm thick) to a lower surface of the first fabric substrate layer 1 and an upper surface of the second fabric substrate layer 2.

a step of constructing electrodes: using conductive ink as electrodes, silk-screen printing the conductive ink to the lower surface of the first fabric substrate layer 1 and the upper surface of the second fabric substrate layer to form a first electrode 4 and a second electrode 5, with a printed pattern of the electrodes being regular grid lines.

a step of connecting an cable 6: using a copper strip with adhesive/a conductive fabric with adhesive to fix the cable 6 to the first electrode 4, and using a copper strip with adhesive/a conductive fabric with adhesive to fix the cable 6 to the second electrode 5;

or, opening eyeholes/eyelets on the first electrode 4 and the second electrode 5, and fixing the cable 6 to the first electrode 4 or the second electrode 5 via fixing parts and the eyeholes/eyelets;

a step of preparing a fabric barrier layer 3: using a fabric mesh with regular through holes 30 as a fabric barrier layer 3 (with flexible film), where the fabric mesh is 2 mm thick and the size of the through holes 30 is 8 mm.

assembling: placing the fabric barrier layer 3 to an upper surface of the second fabric substrate layer 2 component, and the first fabric substrate layer 1 component to a top of the fabric barrier layer 3, with the first electrode 4 facing the fabric barrier layer 3; aligning an edge of the first fabric substrate layer 1 with an edge of the second fabric substrate layer 2 or aligning the first electrode 4 with the second electrode 5. Pressing TPU on the fabric by a hot press and rolling on the edges of the first fabric substrate layer 1 and the second fabric substrate layer 2. Meanwhile, cementing and fixing the TPU on an edge of the fabric barrier layer 3 to the substrate by means of rolling compaction. Trimming edges of the sensing pad after cooling.

Embodiment 2: A Flexible Pressure-Sensing Pad, as Shown in FIG. 4~FIG. 6

The flexible pressure-sensing pad is manufactured by a following method:

Preparing a substrate layer fabric: In this embodiment, a fabric in a size of 1600 mm×500 mm is used as a fabric substrate layer, and the fabric is symmetrically folded to form an upper layer fabric in a size of 800 mm×500 mm as a first fabric substrate layer 1, and a lower layer fabric in a size of 800 mm×500 mm as a second fabric substrate layer 2. The fabric has two sides, a smooth surface is used to form an external surface of a sensing pad, and a relatively coarse surface is used to form an internal surface of the sensing pad.

a step of constructing a flexible film: hot pressing a layer of TPU (100 μm thick) to an upper surface of the first fabric substrate layer 1 and a lower surface of the second fabric substrate layer 2.

a step of constructing electrodes: The first electrode 4 is made of a conductive fabric, conductors on the conductive fabric are 5 mm wide, a distance between adjacent conductors is 5 mm, and the conductors form an interlaced pattern. The conductive fabric is pasted to a lower surface of the first fabric substrate layer 1. The second electrode 5 is made of a conductive fabric, conductors on the conductive fabric are parallel lines approximately forming a right angle with the first electrode 4, and the conductive fabric is pasted on an upper surface of the second fabric substrate layer 2.

a step of connecting an cable 6: using a copper strip with adhesive/a conductive fabric with adhesive to fix the cable 6 to the first electrode 4, and using a copper strip with adhesive/a conductive fabric with adhesive to fix the cable 6 to the second electrode 5;

or, opening eyeholes/eyelets on the first electrode 4 and the second electrode 5, and fixing the cable 6 to the first electrode 4 or the second electrode 5 via fixing parts and the eyeholes/eyelets;

a step of preparing a fabric barrier layer: using a 0.2 mm thick fabric mesh as a fabric barrier layer 3 (with flexible film).

assembling: placing the fabric barrier layer 3 to an upper surface of the second fabric substrate layer 2, and folding the entire fabric along a middle line so that a short edge of the first fabric substrate layer 1 (500 mm) is aligned with a short edge of the second fabric substrate layer 2, or the first electrode 4 is aligned with the second electrode 5 and the fabric barrier layer 3 is between the first fabric substrate layer 1 and the second fabric substrate layer 2. Pressing TPU on the fabric by a hot press and rolling on the edges of the first fabric substrate layer 1 and the second fabric substrate layer 2; meanwhile, cementing and fixing the TPU on an edge of the fabric barrier layer 3 to the first fabric substrate layer 1 or the second fabric substrate layer 2 by means of rolling compaction; trimming edges of the sensing pad after cooling.

Effect Evaluation and Performance Detection

1. The activation thresholds of the flexible pressure-sensing pads in Embodiments 1~2 are detected. Nine testing points are randomly selected on the flexible pressure-sensing pads in Embodiments 1~2 to measure activation thresholds of the flexible pressure-sensing pads in Embodiments 1~2. Pressing area is supposed to be 2 cm$^2$, and detection items and results are shown in Table 1.

TABLE 1

Results of activation thresholds of the flexible pressure-sensing pad in Embodiments 1~2

| Force threshold/N | Embodiment 1 | Embodiment 2 |
| --- | --- | --- |
| Test point 1 | 35.2N | 12.1N |
| Test point 2 | 28.2N | 7.8N |
| Test point 3 | 39.8N | 10.7N |
| Test point 4 | 38.1N | 13.4N |
| Test point 5 | 36.5N | 12.8N |
| Test point 6 | 23.6N | 14.5N |
| Test point 7 | 25.7N | 18.3N |
| Test point 8 | 27.1N | 12.7N |
| Test point 9 | 34.2N | 13.2N |
| Average activation threshold/N | 32.0N | 12.8N |

The foregoing implementation manners are only preferred implementation manners of the present invention and cannot be used to limit the scope of protection of the present invention. Any substantial change and replacement made by those skilled in the art on the basis of the present invention shall fall within the scope of protection required by the present invention.

What is claimed is:

1. A flexible pressure-sensing pad comprising a first fabric substrate layer, a second fabric substrate layer, and a fabric barrier layer provided between the first fabric substrate layer and the second fabric substrate layer; the first fabric substrate layer comprising a first electrode on a side facing toward the fabric barrier layer, and the second fabric substrate layer comprising a second electrode on a side facing toward the fabric barrier layer; the fabric barrier layer comprising multiple through holes; the first electrode and the second electrode are electrically connected with a controller, the first electrode and the second electrode are capable to contact each other via the through holes of the fabric barrier layer.

2. The flexible pressure-sensing pad of claim 1, wherein the first fabric substrate layer and the second fabric substrate layer are two separate fabrics in a same size with one being superimposed on the other, or are one fabric folded symmetrically from a middle line of the fabric.

3. The flexible pressure-sensing pad of claim 1, wherein fabrics for the first fabric substrate layer and the second fabric substrate layer are one of flexible or bendable synthetic textile, vegetable textile, animal textile and mineral textile.

4. The flexible pressure-sensing pad of claim 1, wherein the first electrode covers a lower surface of the first fabric substrate layer, and the second electrode covers an upper surface of the second fabric substrate layer; or the first electrode is distributed on the lower surface of the first fabric substrate layer in a form of parallel lines, cross lines or grid lines, and the second electrode is distributed on the upper surface of the second fabric substrate layer in a form of parallel lines, cross lines or grid lines.

5. The flexible pressure-sensing pad of claim 1, wherein the first electrode and the second electrode both are formed by applying a conductive material to the first fabric substrate layer and the second fabric substrate layer; the conductive material is conductive ink printed on the first fabric substrate layer and the second fabric substrate layer or a solid flexible conductive material adhered to the first fabric substrate layer and the second fabric substrate layer.

6. The flexible pressure-sensing pad of claim 5, wherein the conductive ink is metal Ag, metal Cu, metal Au, carbon or conductive polymer or a composition of more than one of them; the solid flexible conductive material is a conductive fabric or a thin metal strap.

7. The flexible pressure-sensing pad of claim 1, wherein the fabric barrier layer is 0.01 mm-10 mm thick; the through holes of the fabric barrier layer are round holes, triangular holes, rectangular holes, pentagonal holes, hexagonal holes or irregular holes, or a combination of more than one of them.

8. The flexible pressure-sensing pad of claim 1, wherein the flexible pressure-sensing pad further comprises a first flexible film provided between the first fabric substrate layer and the first electrode, and a second flexible film provided between the second fabric substrate layer and the second electrode.

9. The flexible pressure-sensing pad of claim 8, wherein the first flexible film and the second flexible film are 10 μm-500 μm thick thermoplastic films; the thermoplastic films are made of one of TPU, PET and PE.

10. The flexible pressure-sensing pad of claim 8, wherein the flexible pressure-sensing pad further comprises a third flexible film provided around an edge of the first fabric substrate layer and around an edge of the second fabric substrate layer, as a sealing edge cover.

11. A manufacturing method of a flexible pressure-sensing pad, wherein the method comprises, laminating a first flexible film on a first fabric substrate layer, and a second flexible film on a second fabric substrate layer;

laminating a first electrode on the first flexible film and facing away from the first fabric substrate layer, and a second electrode on the second flexible film and facing away from the second fabric substrate layer;

connecting a cable with the first electrode and the second electrode;

assembling the first fabric substrate layer laminated with the first flexible film and the first electrode, a fabric barrier layer, and the second fabric substrate layer laminated with the second flexible film and the second electrode; the fabric barrier layer being between the first electrode and the second electrode, the fabric barrier layer comprising multiple through holes and the first electrode and the second electrode are capable to contact each other via the through holes of the fabric barrier layer.

12. The manufacturing method of a flexible pressure-sensing pad of claim 11 further comprising a step of providing the first fabric substrate layer and the second fabric substrate layer, the step of providing comprising:

preparing a fabric, cleaning the fabric, then cutting the fabric into two fabrics of a same shape and a same size as a first fabric substrate layer and a second fabric substrate layer respectively;

or, using a fabric and symmetrically folding the fabric from a middle line to form the first fabric substrate layer and the second fabric substrate layer.

13. The manufacturing method of a flexible pressure-sensing pad of claim 11, wherein the step of laminating the first flexible film on the first fabric substrate layer, and the second flexible film on the second fabric substrate layer comprises:

pasting thermoplastic films on a lower surface of the first fabric substrate layer and an upper surface of the second fabric substrate layer respectively.

14. The manufacturing method of a flexible pressure-sensing pad of claim 11, wherein the step of laminating the first electrode on the first flexible film and facing away from the first fabric substrate layer, and the second electrode on the second flexible film and facing away from the second fabric substrate layer comprises:

applying conductive ink to the lower surface of the first fabric substrate layer and the upper surface of the second fabric substrate layer by an adhesive or silk-screen printing to form the first electrode and the second electrode; or, printing a solid flexible conductive material to the lower surface of the first fabric substrate layer and the upper surface of the second fabric substrate layer by an adhesive or hot pressing or silk-screen printing to form the first electrode and the second electrode.

15. The manufacturing method of a flexible pressure-sensing pad of claim 11, wherein the step of connecting a cable with the first electrode and the second electrode comprises:

using a copper strip with adhesive/a conductive fabric with adhesive to fix the cable to the first electrode, and using a copper strip with adhesive/a conductive fabric with adhesive to fix the cable to the second electrode;

or, opening eyeholes/eyelets on the first electrode and the second electrode, and fixing the cable to the first electrode or the second electrode via fixing parts and the eyeholes/eyelets.

16. The manufacturing method of a flexible pressure-sensing pad of claim 11, wherein the step of assembling comprises:

placing the barrier layer between the first fabric substrate layer and the second fabric substrate layer, aligning edges of the first fabric substrate layer and the second fabric substrate layer or the first electrode and the second electrode; and then fixing the first fabric substrate layer coated with the first flexible film and the first electrode, the second fabric substrate layer coated with the second flexible film and the second electrode, and the barrier layer together.

* * * * *